US010258224B2

(12) United States Patent
Suehara

(10) Patent No.: US 10,258,224 B2
(45) Date of Patent: Apr. 16, 2019

(54) ACTUATING MEMBER AND MEDICAL DEVICE

(71) Applicant: Terumo Kabushiki Kaisha, Tokyo (JP)

(72) Inventor: Satoru Suehara, Kaisei-machi (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 577 days.

(21) Appl. No.: 14/871,369

(22) Filed: Sep. 30, 2015

(65) Prior Publication Data

US 2016/0015250 A1 Jan. 21, 2016

Related U.S. Application Data

(63) Continuation of application No. PCT/JP2013/059915, filed on Apr. 1, 2013.

(51) Int. Cl.
*A61B 1/005* (2006.01)
*A61B 17/34* (2006.01)
(Continued)

(52) U.S. Cl.
CPC .......... *A61B 1/0057* (2013.01); *A61B 1/0052* (2013.01); *A61B 17/34* (2013.01);
(Continued)

(58) Field of Classification Search
CPC .......... A61M 25/0136; A61M 25/1038; A61M 25/0147; A61M 25/0133; A61B 1/0057;
(Continued)

(56) References Cited

U.S. PATENT DOCUMENTS 5,358,478 A * 10/1994 Thompson ........ A61M 25/0136
604/528
5,861,024 A * 1/1999 Rashidi .............. A61B 18/1492
600/374
(Continued)

FOREIGN PATENT DOCUMENTS

JP S63-035223 A 2/1988
JP H05-507212 A 10/1993
(Continued)

OTHER PUBLICATIONS

International Search Report dated Apr. 23, 2013 issued in PCT/JP2013/059915.

*Primary Examiner* — Emily L Schmidt
*Assistant Examiner* — Leah J Swanson
(74) *Attorney, Agent, or Firm* — Foley & Lardner LLP

(57) ABSTRACT

An actuating member for making a flexible elongate member for medical use perform a predetermined action includes a push/pull member, an operating member, and an advancing member. The push/pull member includes a first moving portion and a second moving portion, which are movable relative to each other. The push/pull member is pushed/pulled in conjunction with a movement of the first moving portion and the second moving portion. The operating member effects the movement of the first moving portion and the second moving portion. The advancing member includes a narrowed portion that moves the first moving portion and the second moving portion in conjunction with an operation of the operating member. The push/pull member makes the elongate member perform at least one of (i) an advance/retraction action and (ii) a bending action by transmitting the movement of the first moving portion and the second moving portion to the elongate member.

5 Claims, 10 Drawing Sheets

(51) Int. Cl.
*A61M 25/01* (2006.01)
*A61B 17/00* (2006.01)
*A61B 90/00* (2016.01)

(52) U.S. Cl.
CPC ..... *A61B 17/3421* (2013.01); *A61M 25/0147* (2013.01); *A61B 2017/00309* (2013.01); *A61B 2017/00327* (2013.01); *A61B 2090/3937* (2016.02); *A61M 25/0136* (2013.01); *A61M 25/0138* (2013.01)

(58) Field of Classification Search
CPC .............. A61B 1/0052; A61B 17/3421; A61B 2017/003; A61B 2017/00318; A61B 2017/00323; A61B 2017/00327
See application file for complete search history.

(56) References Cited

U.S. PATENT DOCUMENTS

| | | |
|---|---|---|
| 2005/0107737 A1 | 5/2005 | McDaniel |
| 2008/0103520 A1* | 5/2008 | Selkee .............. A61M 25/0136 606/195 |
| 2008/0139886 A1 | 6/2008 | Tatsuyama |

FOREIGN PATENT DOCUMENTS

| | | |
|---|---|---|
| JP | 2005-144188 A | 6/2005 |
| JP | 2006-061176 A | 3/2006 |
| JP | 2008-142199 A | 6/2008 |
| WO | WO-91/011213 A1 | 8/1991 |

* cited by examiner

ACTUATING MEMBER AND MEDICAL DEVICE

CROSS-REFERENCE TO RELATED PATENT APPLICATION

This application is a continuation application of and claims the benefit of priority from International Patent Application No. PCT/JP2013/059915, filed Apr. 1, 2013, the contents of which are incorporated herein by reference in their entirety.

BACKGROUND

The present disclosure relates to an actuating member for making a medical elongate member perform a predetermined action, and a medical device equipped with the actuating member.

In the medical field, a flexible elongate member is generally used as a medical device for performing administration of medicine into a living body, suction or injection of various fluids, introduction of other medical devices into the living body, or the like. For example, where an elongate member is used for the introduction of other medical devices, prior to the introduction of the medical device, the elongate member is inserted into a lumen (a blood vessel, a body cavity, or the like) of the living body, and is guided to a target area, such as an area to be treated and its peripheral area. In order to appropriately guide the elongate member to the target area during such use, it is often necessary to introduce the elongate member along a curved path like the lumen of the living body. For this reason, the elongate member may include an actuating member capable of performing a bending operation by a user's proximal operation when the elongate member is used.

As to techniques related to this, Japanese Patent Laid-Open No. 2008-142199 (hereinafter referred to as "Patent Document 1") describes an actuating member that includes a push/pull member connected to an elongate member, a pulley around which the push/pull member is wound, a handle for rotationally actuating the pulley, and an endoscope into which the actuating member is assembled. In this actuating member, the handle is arranged on a proximal side of the endoscope and rotates around an axis orthogonal to the axial direction of the elongate member, thereby winding the push/pull member to perform a bending action.

SUMMARY

In the actuating member of Patent Document 1, the push/pull member is arranged so as to be wound around the pulley and an action direction in which the push/pull member is pushed/pulled is converted from a straight direction into a circumferential direction for bending. Therefore, a wire with a relatively small rigidity or the like is used as the push/pull member. For this reason, there is a possibility that a push/pull force will not be reliably transmitted to the elongate member via this wire.

Additionally, because it is necessary to wind the wire around the pulley with good followability, the pulley must be large, causing the entire device to be large.

Disclosed herein is an actuating member by which an advance/retraction movement of a push/pull member can be efficiently transmitted to an elongate member and which enables a medical device to be reduced in overall size, and a medical device equipped with the actuating member.

The object of certain embodiments the present disclosure will be achieved by any one of the followings.

In one aspect, an actuating member for making a flexible elongate member for medical use perform a predetermined action includes a push/pull member, an operating member, and an advancing member. The push/pull member includes a first moving portion and a second moving portion which are disposed on a proximal side along an axial direction of the elongate member and which are movable relative to each other in the axial direction of the elongate member. The push/pull member further includes a first extending portion that extends from the first moving portion toward a distal side along the axial direction of the elongate member; and a second extending portion that extends from the second moving portion toward the distal side along the axial direction of the elongate member. The push/pull member is pushed/pulled in the axial direction of the elongate member in conjunction with a movement of the first moving portion and the second moving portion. The operating member effects the movement of the first moving portion and the second moving portion. The advancing member includes a narrowed portion that gradually narrows toward an end portion and that advances in between the first moving portion and the second moving portion in conjunction with the operation of the operating member to thereby move the first moving portion and the second moving portion. The push/pull member is capable of making the elongate member perform at least one of (i) an advance/retraction action and (ii) a bending action by transmitting the movement of the first moving portion and the second moving portion, which are moved by the advancing member, to the elongate member.

According to the actuating member configured as above, the push/pull member is pushed/pulled in the axial direction of the elongate member, without conversion of its action direction, and the elongate member is thereby made to perform an advance/retraction action or a bending action. Therefore, the advance/retraction movement of the push/pull member can be efficiently transmitted to the elongate member. In addition, because it is unnecessary to wind the push/pull member around the operating member, a medical device reduced in overall size can be realized.

In the actuating member as above, the advancing member may be configured to move the first moving portion and the second moving portion in opposite directions along the axial direction, and the movement of the first moving portion and the second moving portion makes the elongate member perform the bending action.

According to this configuration, the first moving portion and the second moving portion are moved in the opposite directions to thereby make the elongate member perform a bending action. Therefore, the elongate member can be bent with reduced traveling distances of the first moving portion and the second moving portion. Consequently, operability of the actuating member is enhanced.

In the actuating member as above, the advancing member may be configured to advance/retract in a direction intersecting the axial direction, and advance/retraction of the advancing member makes the narrowed portion advance/retract.

According to this configuration, advance/retraction of the advancing member makes the narrowed portion advance/retract. Therefore, the narrowed portion can be made to advance in between the first moving portion and the second moving portion, to thereby bend the elongate member, with a simple configuration. As a consequence, a smaller medical device can be realized.

In the actuating member as above, the operating member may be composed of a tube-shaped member, which includes a thin-walled portion and a thick-walled portion thicker than the thin-walled portion. The operating member may accommodate the advancing member therein and rotation of the operating member makes the advancing member advance/retract.

According to this configuration, because the operating member is composed of the tube-shaped member having the thin-walled portion and the thick-walled portion, the advancing member can be made to advance/retract by rotating the operating member. Therefore, the operability of the actuating member can be further enhanced.

In the actuating member as above, the advancing member may be configured to rotate in a circumferential direction of the elongate member, and the rotation of the advancing member makes the narrowed portion advance/retract.

According to this configuration, rotation of the advancing member in the circumferential direction makes the narrowed portion advance/retract. Therefore, the narrowed portion can be made to advance in between the first moving portion and the second moving portion to thereby bend the elongate member with a simple configuration. Consequently, a medical device may be further reduced in overall size.

In the actuating member as above, the operating member may be composed of a tube-shaped member that is formed at an inner peripheral surface thereof with the advancing member in a circumferential direction, and rotation of the operating member makes the advancing member rotate.

According to this configuration, because the operating member is composed of the tube-shaped member, which is formed at an inner peripheral surface thereof with the advancing member in the circumferential direction, the advancing member can be made to advance/retract by rotating the operating member. Therefore, the operability of the actuating member can be further enhanced.

In the actuating member as above, the advancing member may be configured to move the first moving portion and the second moving portion in the same direction along the axial direction with different traveling distances, and the movement of the first moving portion and the second moving portion makes the elongate member perform both the advance/retraction action and the bending action.

According to this configuration, moving the first moving portion and the second moving portion in the same direction makes the elongate member perform a bending action. Therefore, the elongate member can be made to perform a bending action while performing an advance/retraction action. As a consequence, the performance of an actuating member may be further enhanced.

In the actuating member as above, the advancing member may be configured to rotate in a circumferential direction of the elongate member, and the rotation of the advancing member makes the narrowed portion advance/retract.

According to this configuration, rotation of the advancing member in the circumferential direction makes the narrowed portion advance/retract. Therefore, the narrowed portion can be made to advance in between the first moving portion and the second moving portion to thereby bend the elongate member with a simple configuration. Consequently, the medical device can be further reduced in overall size.

In the actuating member as above, the operating member may be composed of a tube-shaped member having the advancing member formed spirally at an inner peripheral portion thereof, and rotation of the operating member makes the advancing member rotate.

According to this configuration, the operating member is composed of the tube-shaped member formed with the advancing member spirally at an inner peripheral portion thereof. Therefore, the advancing member can be made to advance/retract by rotating the operating member. In consequence, the operability of the actuating member can be further enhanced.

The actuating member as above may further include a visual recognition portion, which enables at least a bending amount, of an advance/retraction amount and the bending amount of the elongate member, to be confirmed by visual recognition.

According to this configuration, at least the bending amount of the advance/retraction amount and the bending amount of the elongate member can be confirmed by visual recognition. Therefore, the operability of the actuating member is enhanced.

In another aspect, a medical device includes the actuating member as above and a flexible elongate member. The actuating member makes the flexible elongate member perform at least one of (i) an advance/retraction action and (ii) a bending action.

According to this aspect, it is possible to provide a medical device equipped with an actuating member by which advance/retraction movement of a push/pull member can be efficiently transmitted to an elongate member and a medical device with a reduced overall size can be realized.

DETAILED DESCRIPTION OF THE PREFERRED EMBODIMENTS

Figure 1:
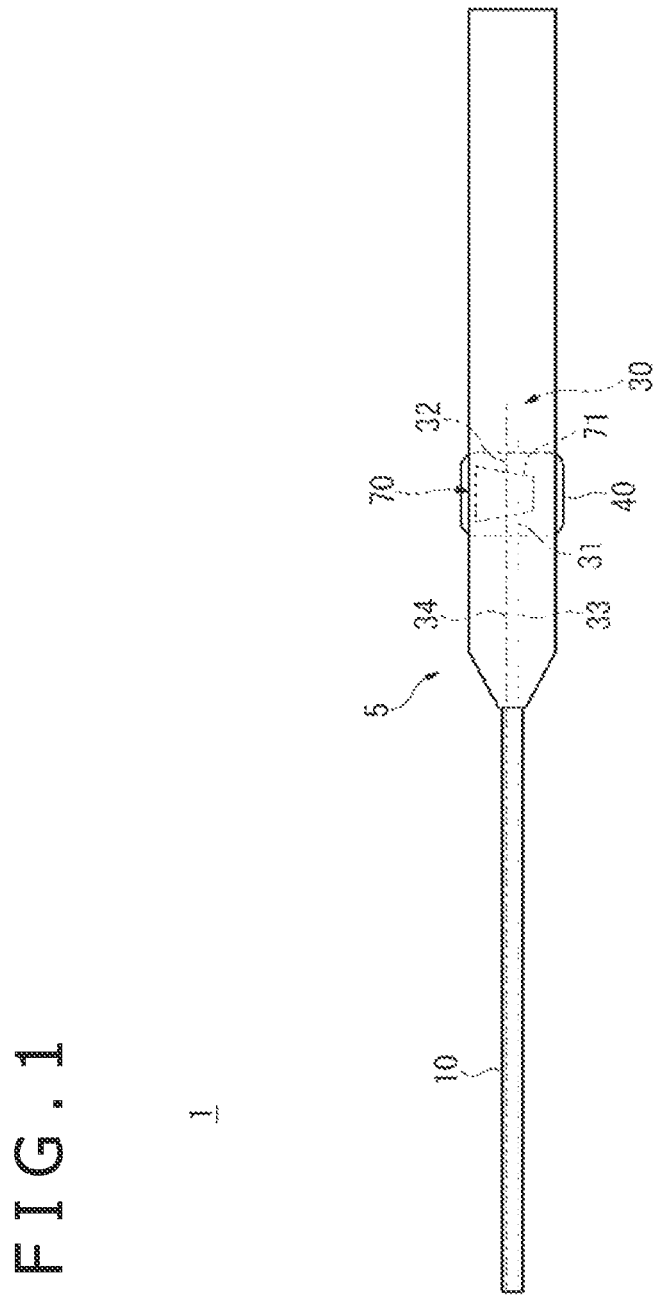
FIG. 1 is a schematic view of a medical device according to a first embodiment of the present disclosure.

Preferred embodiments of the present disclosure will be described below, referring to the drawings. Note that dimensional ratios in the drawings may be exaggerated for convenience of explanation and may therefore be different from the actual ratios. In the following description, the operator's proximal side of a medical device according to each embodiment of the present disclosure will be referred to as the "proximal side," and the side of insertion into a living body lumen will be referred to as the "distal side."

First Embodiment

The configuration of a medical device 1 according to a first embodiment of the present disclosure will be described.

Figure 2:
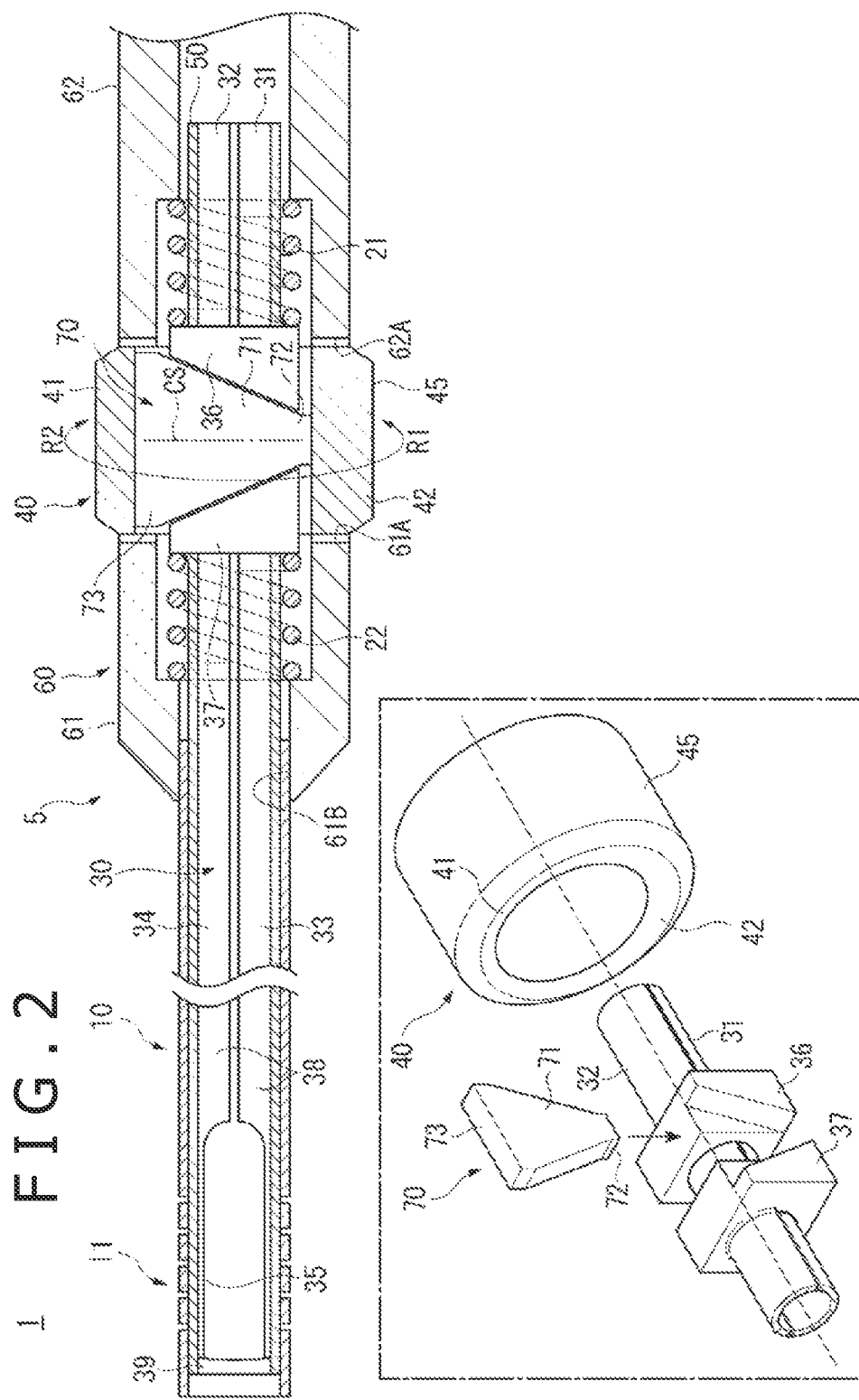
FIG. 2 is a side sectional view of the medical device according to the first embodiment.

FIG. 1 is a schematic view of the medical device 1 according to the first embodiment of the present disclosure. FIG. 2 is a side sectional view of the medical device 1 according to the first embodiment.

The medical device 1 according to the first embodiment of the present disclosure, as shown in FIG. 1, includes a flexible elongate member 10 for medical use, and an actuating member 5 for making the elongate member 10 perform a predetermined action. The actuating member 5 has a push/pull member 30, which includes a plurality of divided portions 38 to be described later. The push/pull member 30 also includes a first moving portion 31 and a second moving portion 32, which are disposed on a proximal side along an axial direction of the elongate member 10 and which are movable relative to each other in the axial direction of the elongate member 10. A first extending portion 33 extends from the first moving portion 31 toward a distal side along the axial direction of the elongate member 10, and a second extending portion 34 extends from the second moving portion 32 toward the distal side along the axial direction of the elongate member 10. The push/pull member 30 is pushed/pulled in the axial direction of the elongate member 10 in conjunction with movement of the first moving portion 31 and the second moving portion 32. The actuating member 5 further includes an operating member 40 for effecting a movement of the first moving portion 31 and the second moving portion 32, and an advancing member 70, which includes a narrowed portion 71 that gradually narrows toward an end portion. The narrowed portion 71 advances in between the first moving portion 31 and the second moving portion 32, in conjunction with an operation of the operating member 40, to thereby move the first moving portion 31 and the second moving portion 32. The push/pull member 30 is capable of making the elongate member 10 perform a bending action by transmitting the movement of the first moving portion 31 and the second moving portion 32, which are moved by the advancing member 70, to the elongate member 10. This will be detailed below.

As shown in FIG. 2, the actuating member 5 includes the push/pull member 30, which is pushed/pulled in the axial direction of the elongate member 10 in conjunction with movement of the first moving portion 31 and the second moving portion 32, the operating member 40, which effects movement of the first moving portion 31 and the second moving portion 32, and the advancing member 70 provided with the narrowed portion 71, which is capable of advancing in between the first moving portion 31 and the second moving portion 32 in conjunction with an operation of the operating member 40. The actuating member 5 further includes a sealing portion 50, which is provided at an outer periphery of the push/pull member 30 and which seals a fluid flowing within the push/pull member 30, a base portion 60, which is provided at the outer periphery on the proximal side of the sealing portion 50 and which supports the push/pull member 30 and the operating member 40, and a visual recognition portion 45, which enables a bending amount (bending angle) of the elongate member 10 to be confirmed by visual recognition.

Figure 3:
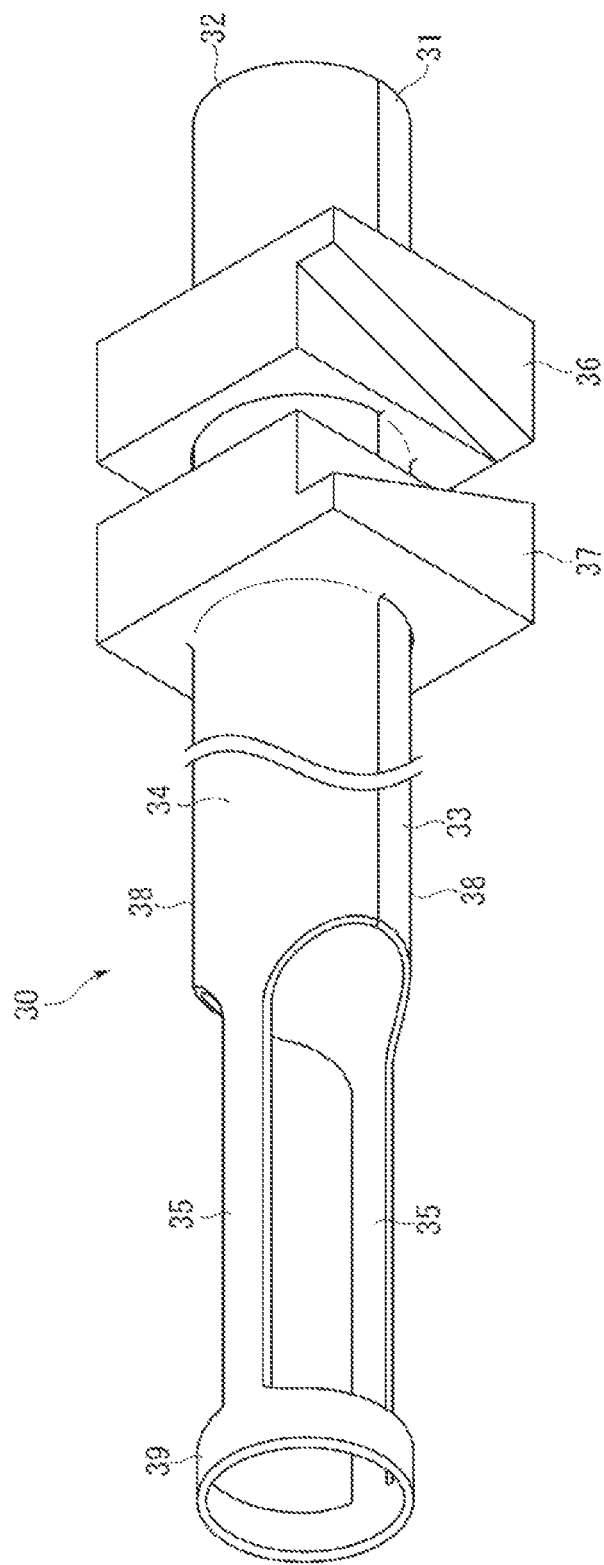
FIG. 3 is a perspective view of a push/pull member.

FIG. 3 is a perspective view of the push/pull member 30.

As also shown in FIG. 3, the push/pull member 30 includes the plurality of divided portions 38, which are divided in the circumferential direction and which together form a tube-shaped structure. An annular connecting portion 39 connects tips (regarding the axial direction) of the divided portions 38. In conjunction with movement of the first moving portion 31 and the second moving portion 32, the divided portions 38 are pushed/pulled in the axial direction of the elongate member 10, thereby making the elongate member 10 perform a bending action.

The divided portions 38 include the first moving portion 31 and the second moving portion 32, which are disposed on the proximal side regarding the axial direction of the elongate member 10 and which are movable relative to each other along the axial direction of the elongate member 10. The divided portions 38 also include the first extending portion 33, which extends from the first moving portion 31 toward the distal side of the elongate member 10 in the axial direction, the second extending portion 34, which extends from the second moving portion 32 toward the distal side of the elongate member 10 in the axial direction, and bending portions 35, which are provided on the distal side of the first extending portion 33 and the second extending portion 34 and which are bent by pushing/pulling of the first extending portion 33 and the second extending portion 34 relative to each other. Note that it is sufficient for the push/pull member 30 to be capable of pushing/pulling the distal side of the elongate member 10, and, therefore, the push/pull member 30 may be, for example, a traction wire, a plate-shaped belt member or the like.

The first moving portion 31 has a first sliding contact portion 36 with which the advancing member 70 makes sliding contact. The first sliding contact portion 36 is provided to circumferentially surround the first moving portion 31 and the second moving portion 32 and is fixed to a peripheral surface of the first moving portion 31. In addition, the first sliding contact portion 36 retains the second moving portion 32 so that the second moving portion 32 can advance/retract. The first sliding contact portion 36 is provided on the proximal side relative to the advancing member 70 and is biased toward the advancing member 70 by a first coil spring 21 supported by a gripping portion 62. The first sliding contact portion 36 is provided with a first inclined surface inclined against an orthogonal plane CS (as shown in FIG. 2), which is orthogonal to the axial direction of the elongate member 10. The narrowed portion 71 makes sliding contact with the first inclined surface.

The second moving portion 32 has a second sliding contact portion 37 with which the advancing member 70 makes sliding contact. The second sliding contact portion 37 is provided to circumferentially surround the first moving portion 31 and the second moving portion 32 and is fixed to a peripheral surface of the second moving portion 32. In addition, the second sliding contact portion 37 retains the first moving portion 31 so that the first moving portion 31 can advance/retract. The second sliding contact portion 37 is provided on the distal side relative to the advancing member 70 and is biased toward the advancing member 70 by a second coil spring 22 supported by a supporting portion 61. The second sliding contact portion 37 is provided with a second inclined surface inclined against the orthogonal plane CS. The second inclined surface extends toward the opposite side as compared to the inclined surface of the first sliding contact portion 36. The narrowed portion 71 makes sliding contact with the second inclined surface.

The first extending portion 33 transmits movement of the first moving portion 31 to the bending portion 35.

The second extending portion 34 transmits movement of the second moving portion 32 to the bending portion 35.

The bending portions 35 are each a portion obtained by cutting out circumferential end edges (on the distal side) of the divided portions 38, and are formed to be narrower than the first extending portion 33 and the second extending portion 34.

Because the push/pull member 30 is configured as above, it is ensured that when the first extending portion 33 is located on the distal side compared to the second extending portion 34 due to the movement of the first moving portion and the movement of the second moving portion, the bending portions 35 are bent upward, and when the first extending portion 33 is located on the proximal side compared to the second extending portion 34, the bending portions 35 are bent downward.

As shown in FIG. 2, the operating member 40 is composed of a tube-shaped member having a thin-walled portion 41 and a thick-walled portion 42 thicker than the thin-walled portion 41 in wall thickness. The operating member 40 is provided to accommodate the first moving portion 31, the second moving portion 32, and the advancing member 70 therein. The operating member 40 is so provided that by rotating the operating member 40, it is possible to make the advancing member 70 advance/retract by an operation to effect movement of the first moving portion 31 and the second moving portion 32. In addition, attendant on its rotation, the operating member 40 makes the first moving portion 31 and the second moving portion 32 move relative to each other in close relation, thereby bending the elongate member 10. The operating member 40 has an outer peripheral surface provided with a ruggedness (not shown), so that the operating member 40 is so shaped as to be rotatable by an operator's fingers.

The advancing member 70 is so configured as to be capable of moving the first moving portion 31 and the second moving portion 32 in opposite directions along the axial direction, and movement of the first moving portion 31 and the second moving portion 32 makes the elongate member 10 perform a bending action. The advancing member 70 is formed in a wedge-like shape provided with the narrowed portion 71 and is so provided that it can advance/retract in a direction intersecting the axial direction of the elongate member 10. With the advancing member 70 made to advance/retract, the narrowed portion 71 is made to advance/retract. The advancing member 70 is accommodated in the operating member 40, with the narrowed portion 71 interposed between the first sliding contact portion 36 and the second sliding contact portion 37. In addition, the advancing member 70 is so provided that its end portion 72 on one side of the narrowed portion 71 and its end portion 73 on the other side of the narrowed portion 71 can make sliding contact with an inner surface of the operating member 40.

The sealing portion 50 seals a fluid flowing within the push/pull member 30. The sealing portion 50 is fixed in close contact with an outer periphery of the push/pull member 30. The method for fixation is not particularly limited. For example, fixation may be accomplished by an adhesive, soldering or brazing, welding, or the like. Examples of material usable for the sealing portion 50 include thermoplastic resins, such as fluoro-resins such as ETFE (ethylene-tetrafluoroethylene copolymer), PTFE (polytetrafluoroethylene), etc., polyolefins, such as PE (polyethylene), PP (polypropylene), etc., polyamides, polyesters, polyurethane, etc. which are excellent in biocompatibility. Note that the sealing portion 50 may be disposed inside of the push/pull member 30.

The base portion 60 supports the elongate member 10, the push/pull member 30, and the operating member 40. The base portion 60 includes the supporting portion 61, which is disposed on the distal side relative to the operating member 40 and which supports the elongate member 10, the push/pull member 30, and the operating member 40. The base portion 60 also includes the gripping portion 62, which is disposed on the proximal side relative to the operating member 40, supports the push/pull member 30 and the operating member 40, and is gripped when an operator performs a procedure. The base portion 60 is formed of a rigid resin material, for example.

The supporting portion 61 supports the elongate member 10, the push/pull member 30, and the operating member 40. The supporting portion 61 includes a recessed portion 61A provided on the proximal side for accommodating the operating member 40, and an opening portion 61B, which is provided on the distal side and in which the elongate member 10 is inserted.

The gripping portion 62 supports the push/pull member 30 and the operating member 40, and is gripped when an operator performs a procedure. The gripping portion 62 has a recessed portion 62A provided on the distal side for accommodating the operating member 40.

The visual recognition portion 45 is provided on an outer peripheral surface of the operating member 40 and enables a bending amount of the elongate member 10, bent in conjunction with movement of the first moving portion 31 and the second moving portion 32, to be confirmed by visual recognition. The visual recognition portion 45 may be, for example, a marker. However, the visual recognition portion 45 not restricted to a marker, but may also be a scale or the like.

The elongate member 10 is inserted in the opening portion 61B on the proximal side thereof and is bent on the distal side thereof through the bending of the bending portions 35. The elongate member 10 is provided on the distal side thereof with rigidity weakened portions 11, which can be easily bent. In this embodiment, the rigidity weakened portions 11 are each configured as a combination of tube-shaped members formed of a metal, such as stainless steel, which is ordinarily used for an endoscope or the like. The rigidity weakened portions 11 are provided at two positions (an upper position and a lower position), but it is sufficient that the rigidity weakened portion is provided on at least one side. Examples of a material usable for the elongate member 10 include thermoplastic resins, such as fluoro-resins such as ETFE (ethylene-tetrafluoroethylene copolymer), PTFE (polytetrafluoroethylene), etc., polyolefins, such as PE (polyethylene), PP (polypropylene), etc., polyamides, polyesters, polyurethane, etc. which are excellent in biocompatibility. In this case, the rigidity weakened portions 11 may be, but are not restricted to, slits. The rigidity weakened portions 11 may be configured by use of a material lower in rigidity than other portions.

Figure 4:
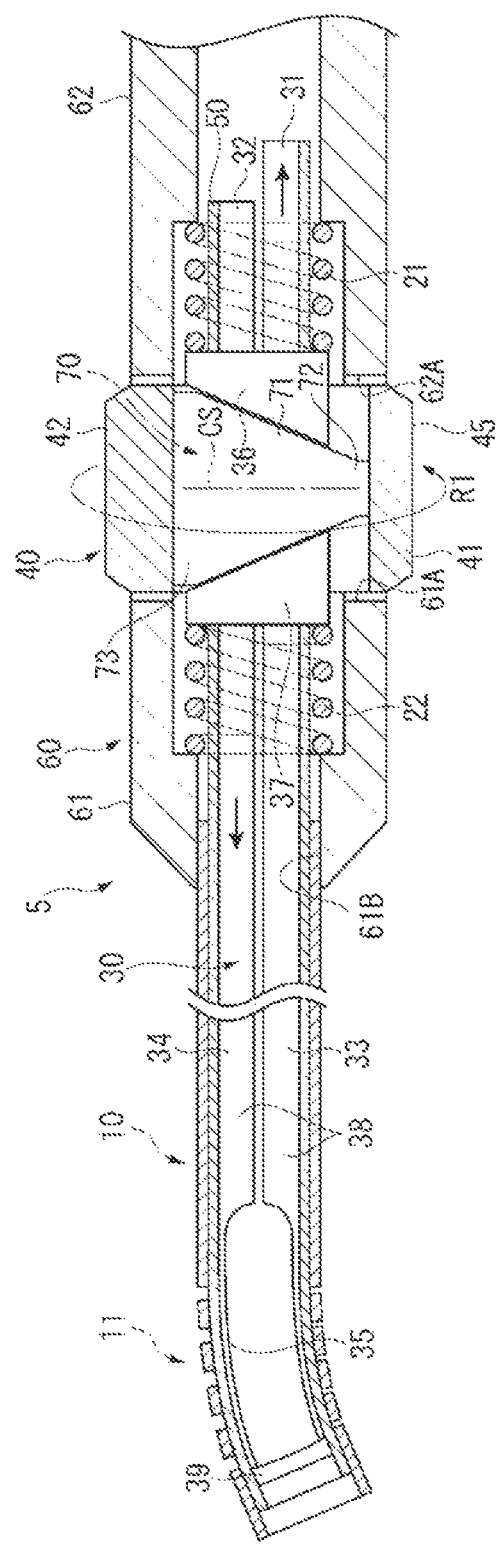
FIG. 4 is a side sectional view showing the medical device when a distal side of an elongate member is bent downward in the first embodiment.

A method of bending the elongate member 10 by the actuating member 5 according to the first embodiment of the present disclosure will be described below, referring to FIG. 4. FIG. 4 is a side sectional view showing the medical device 1 when the distal side of the elongate member 10 is bent downward.

When an operator, as shown in FIG. 4, rotates the operating member 40 in a direction R1, the advancing member 70 is pushed by the thick-walled portion 42 of the operating member 40 toward the thin-walled portion 41, and the narrowed portion 71 advances in between, and while making sliding contact with, the first sliding contact portion 36 and the second sliding contact portion 37. Consequently, the first moving portion 31 is moved toward the proximal side as the first sliding contact portion 36 is pushed in the axial direction by the narrowed portion 71, whereas the second moving portion 32 is moved toward the distal side as the second sliding contact portion 37 is pushed in the axial direction by the narrowed portion 71. As a result, the first extending portion 33 is moved toward the proximal side, whereas the second extending portion 34 is moved toward the distal side. When the first extending portion 33 is moved toward the proximal side and the second extending portion 34 is moved toward the distal side, the bending portions 35 are bent downward. With the bending portions 35 bent downward, the distal side of the elongate member 10 is also bent downward.

Thus, according to the first embodiment of the present disclosure, the push/pull member 30 is pushed/pulled in the axial direction of the elongate member 10, without conversion of its action direction, thereby making the elongate member 10 perform a bending action. Therefore, the advance/retraction movement of the push/pull member 30 can be efficiently transmitted to the elongate member 10. Besides, since it is unnecessary to wind the push/pull member 30 around the operating member 40, the medical device 1 can be made smaller in overall size.

In addition, the operating member 40 is so configured that the first moving portion 31 and the second moving portion 32 can be moved in opposite directions along the axial direction, and movement of the first moving portion 31 and the second moving portion 32 makes the elongate member 10 perform a bending action. Accordingly, the elongate member 10 can be bent with smaller traveling distances of the first moving portion 31 and the second moving portion 32, and operability of the actuating member 5 is enhanced.

Because the narrowed portion 71 is made to advance/retract by making the advancing member 70 advance/retract, the narrowed portion 71 can be made to advance in between the first moving portion 31 and the second moving portion 32 with a simple configuration, thereby bending the elongate member 10. As such, the medical device 1 can be made even smaller in overall size.

Further, because the operating member 40 is composed of the tube-shaped member having the thin-walled portion 41 and the thick-walled portion 42, the advancing member 70 can be made to advance/retract by rotating the operating member 40, so that operability of the actuating member 5 can be further enhanced.

In addition, the actuating member 5 further includes the visual recognition portion 45, which enables the bending amount of the elongate member 10 to be confirmed by visual recognition. Therefore, the bending amount of the elongate member 10 can be confirmed through the visual recognition portion 45, which enhances the operability of the actuating member 5.

In addition, it is possible to provide a medical device 1 equipped with the actuating member 5 by which the advance/retraction movement of the push/pull member 30 can be efficiently transmitted to the elongate member 10 and the medical device can be made smaller in overall size.

Second Embodiment

A second embodiment of the present disclosure will be described below. Descriptions of features common to the first and second embodiments will be omitted, and only features characteristic of the second embodiment will be described.

Figure 5:
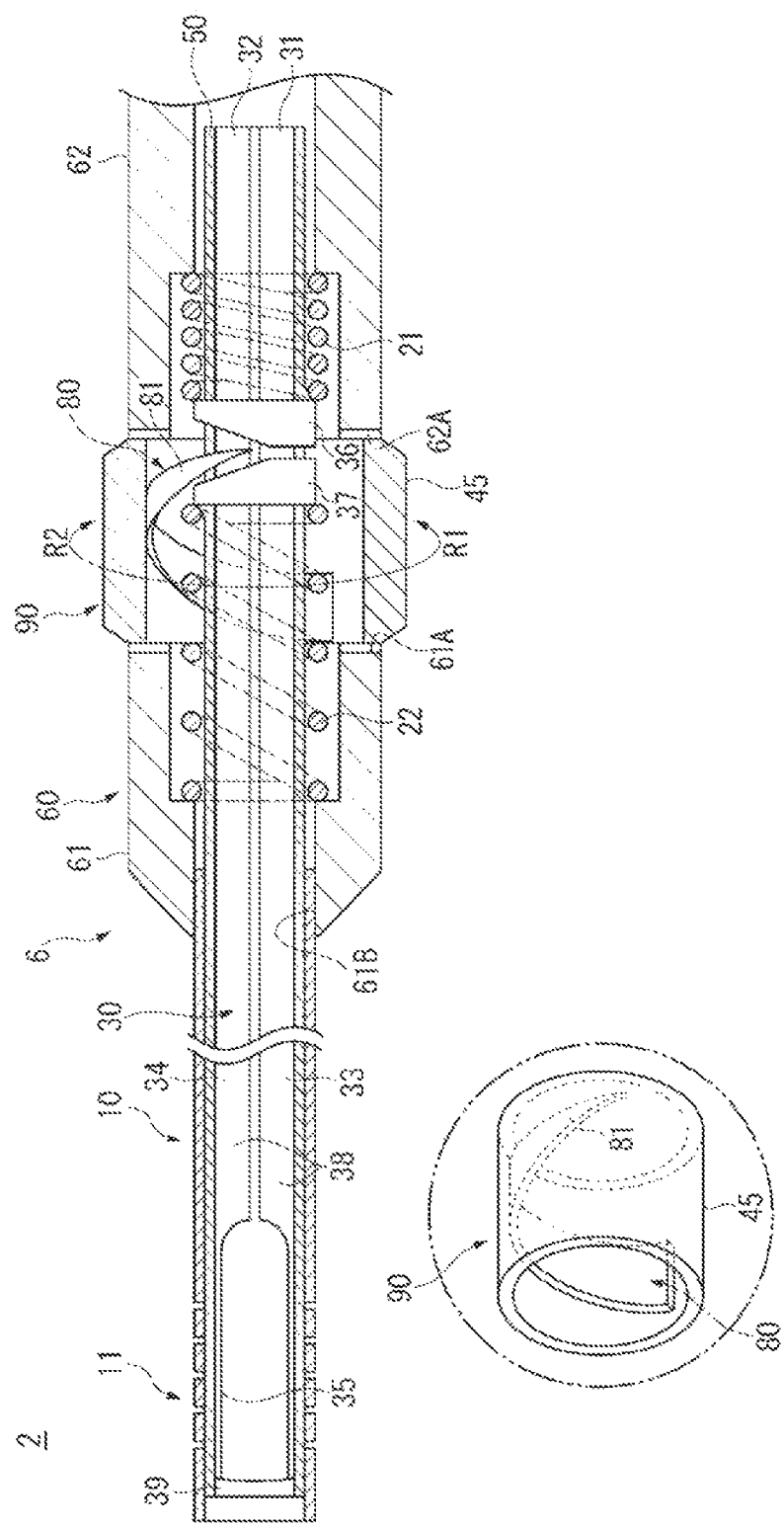
FIG. 5 is a side sectional view of a medical device according to a second embodiment of the present disclosure.

FIG. 5 is a side sectional view of a medical device 2 according to the second embodiment of the present disclosure.

The medical device 2 according to the second embodiment of the present disclosure, as shown in FIG. 5, includes an actuating member 6, which includes an operating member 90 for effecting a movement of a first moving portion 31 and a second moving portion 32, and an advancing member 80 having a narrowed portion 81 that gradually narrows toward an end portion. The narrowed portion 81 is capable of advancing in between the first moving portion 31 and the second moving portion 32 in conjunction with an operation of the operating member 90. The actuating member 6 also includes a visual recognition portion 45, which enables an advance/retraction amount and a bending amount (bending angle) of an elongate member 10 to be confirmed by visual recognition. Other features of the second embodiment are the same as in the first embodiment.

The advancing member 80 is configured to be capable of moving the first moving portion 31 and the second moving portion 32 in the same direction along the axial direction with different traveling directions. With the first moving portion 31 and the second moving portion 32 moved, the elongate member 10 is made to perform an advance/retraction action and a bending action. The advancing member 80 is provided to be rotatable in the circumferential direction of the elongate member 10. With the advancing member 80 made to advance/retract, the narrowed portion 81 is made to advance/retract. The advancing member 80 is provided to extend spirally and is formed in a wedge-like shape, which is gradually narrowed along a spiral direction.

The operating member 90 is composed of a tube-shaped member, which has a uniform wall thickness along the circumferential direction, and is configured to accommodate the first moving portion 31, the second moving portion 32, and the advancing member 80 therein. Rotation of the operating member 90 can make the advancing member 80 advance/retract in order to effect movement of the first moving portion 31 and the second moving portion 32. The operating member 90 is composed of the tube-shaped member formed with the spiral-shaped advancing member 80 at its inner peripheral surface, and rotation of the operating member 90 rotates the advancing member 80.

Figure 6:
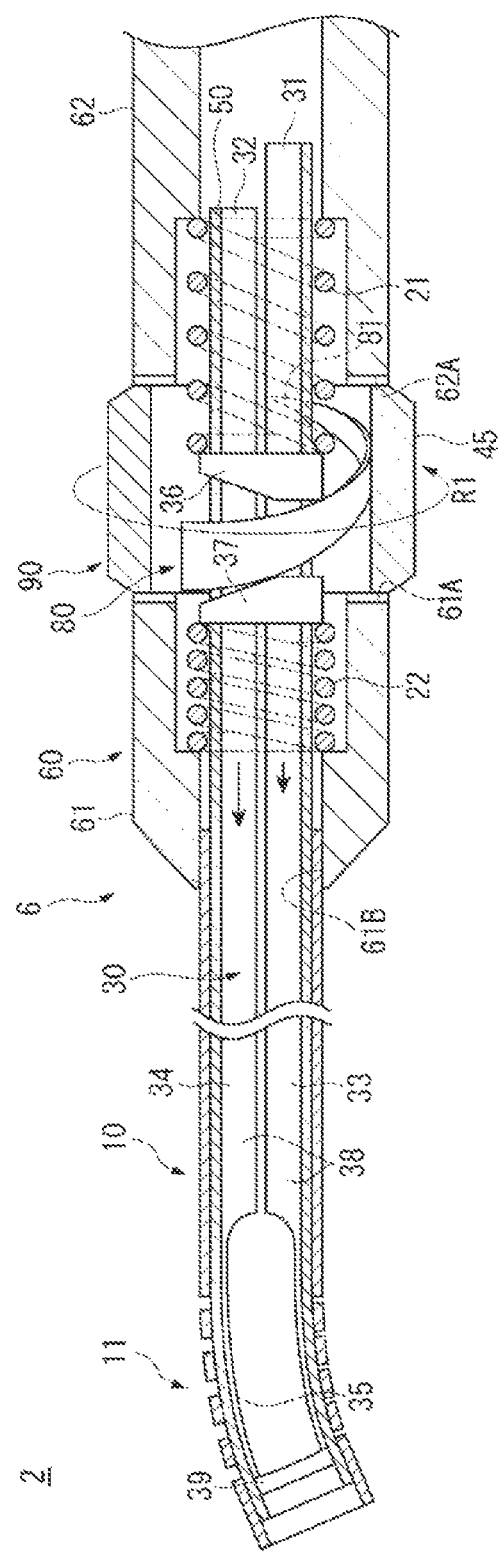
FIG. 6 is a side sectional view showing the medical device when a distal side of an elongate member is bent downward in the second embodiment.

A method of bending the distal side of the elongate member 10 by the actuating member 6 according to the second embodiment of the present disclosure will be described below, referring to FIG. 6. FIG. 6 is a side sectional view showing the medical device 2 when the distal side of the elongate member 10 is bent downward.

An operator, as shown in FIG. 6, rotates the operating member 90 in a direction R1. As a result, the first moving portion 31 is moved toward the distal side while being pressed against the narrowed portion 81 by the first coil spring 21, and the second moving portion 32 is also moved toward the distal side while being pressed by the narrowed portion 81. In this instance, since the advancing member 80 is provided in the spiral shape, while the first moving portion 31 and the second moving portion 32 are both moved toward the distal side, the second moving portion 32 is moved more toward the distal side than the first moving portion 31. Therefore, bending portions 35 are bent downward while being moved toward the distal side. When the bending portions 35 are bent downward while being moved toward the distal side, the distal side of the elongate member 10 is also bent downward while the elongate member 10 is moved toward the distal side.

Thus, according to the second embodiment of the present disclosure, the push/pull member 30 is pushed/pulled in the axial direction of the elongate member 10, without conversion of its action direction, to thereby make the elongate member 10 perform an advance/retraction action and a bending action. Therefore, the advance/retraction movement of the push/pull member 30 can be efficiently transmitted to the elongate member 10. In addition, since it is unnecessary to wind the push/pull member 30 around the operating member 90, the medical device 2 can be made smaller in overall size.

In addition, the operating member 90 is configured to be capable of moving the first moving portion 31 and the second moving portion 32 in the same direction along the axial direction with different traveling distances, and movement of the first moving portion 31 and the second moving portion 32 makes the elongate member 10 perform an advance/retraction action and a bending action. Therefore, an actuating member 6 with enhanced performance can be provided.

Because the rotation of the advancing member 80 in the circumferential direction causes the narrowed portion 81 to advance/retract, the narrowed portion 81 can be made to advance in between the first moving portion 31 and the second moving portion 32 to thereby bend the elongate member 10 with a simple configuration. Accordingly, the medical device 2 can be made further smaller in overall size.

Further, because the operating member 90 is composed of the tube-shaped member formed with the spiral-shaped advancing member 80 at its inner peripheral surface, rotation of the operating member 90 can make the advancing member 80 advance/retract, whereby the operability of the actuating member 6 can be enhanced.

Modification examples of the aforementioned embodiments will be described below by way of example.

FIGS. 7A to 10C are side sectional views of actuating members 5A to 5F of medical devices according to Modification Examples 1 to 6. Note that in FIGS. 7A to 9B, other configurations than the actuating members 5A to 5C are omitted, together with a sealing portion 50, and, in FIGS. 10A to 10C, other configurations than operating members 40D to 40F and advancing members 70 and 70E are omitted.

Modification Example 1

Figure 7A:
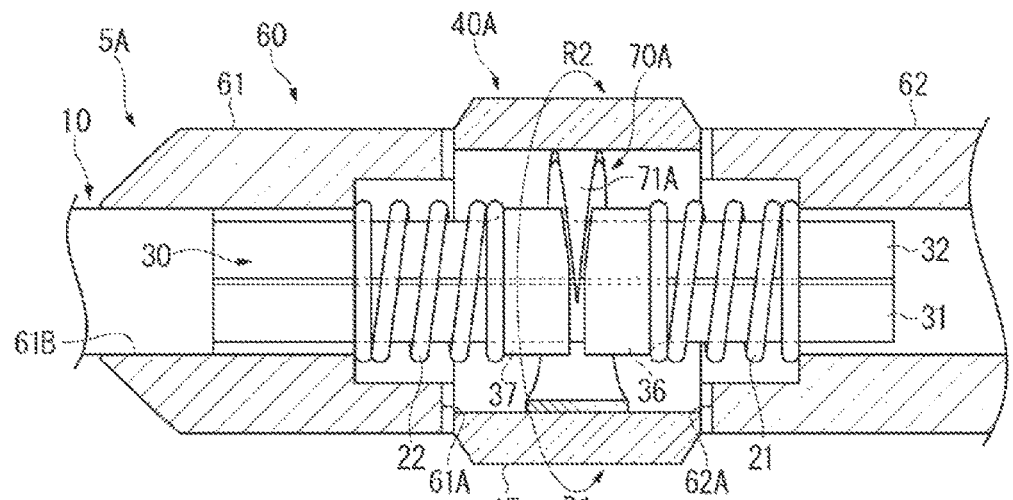
FIGS. 7A and 7B are side sectional views of an actuating member of a medical device according to a Modification Example 1.

The actuating member 5A shown in FIG. 7A differs from the first embodiment in that the actuating member 5A has an operating member 40A and an advancing member 70A.

The advancing member 70A is provided to extend circumferentially and is formed in a wedge-like shape that gradually narrows along the circumferential direction. The advancing member 70A is rotatable in the circumferential direction of an elongate member 10, and rotation of the advancing member 70A makes a narrowed portion 71A advance/retract.

The operating member 40A is composed of a tube-shaped member, which has a uniform wall thickness along the circumferential direction and which is formed with the advancing member 70A at its inner peripheral surface in the circumferential direction. Rotation of the operating member 40A rotates the advancing member 70A.

Figure 7B:
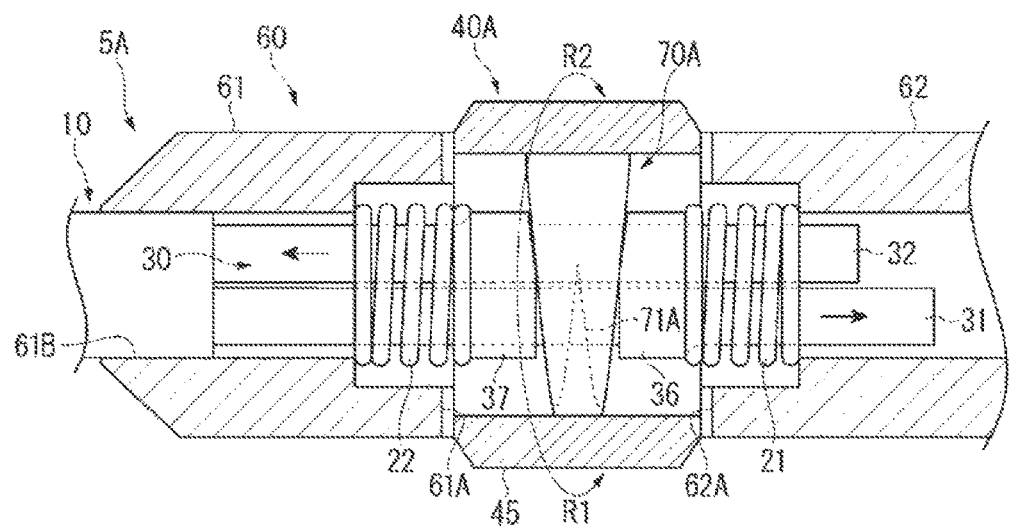

According to this configuration, when the operating member 40A is rotated, the elongate member 10 is bent in the same manner as in the first embodiment. Specifically, when the operating member 40A is rotated in a direction R1, a first moving portion 31 is pressed by the narrowed portion 71A to move toward the proximal side, whereas a second moving portion 32 is pressed by the narrowed portion 71A to move toward the distal side, as shown in FIG. 7B. As a result, bending portions 35 are bent downward, and the distal side of the elongate member 10 is thereby bent downward.

Modification Example 2

Figure 8A:
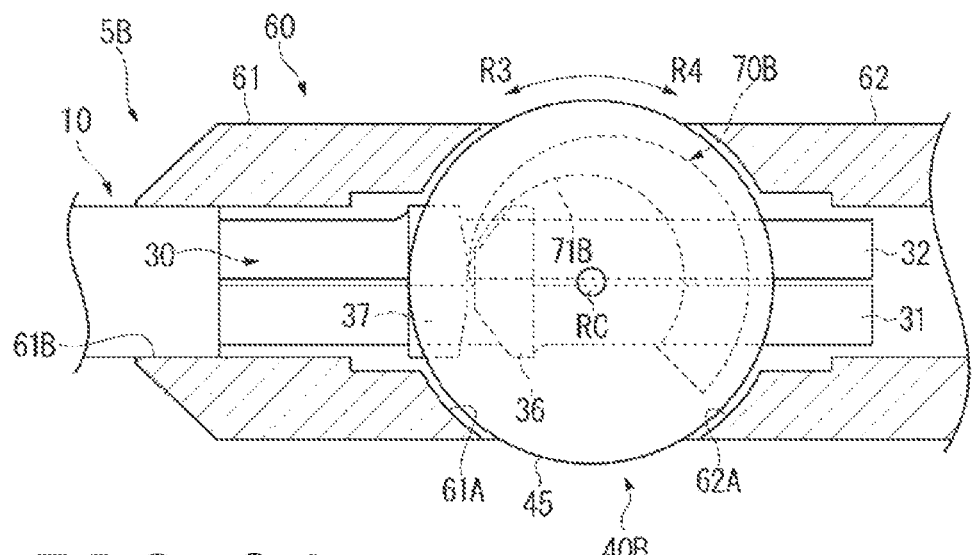
FIGS. 8A and 8B are side sectional views of an actuating member of a medical device according to a Modification Example 2.

The actuating member 5B shown in FIG. 8A differs from the first embodiment in that the actuating member 5B has an operating member 40B and an advancing member 70B.

The operating member 40B is composed of a disk-shaped member, which is provided to be rotatable about a rotational center RC having an axis that intersects the axis of an elongate member 10.

The advancing member 70B is formed integrally with a disk surface of the operating member 40B. The advancing member 70B is provided to extend around a rotational center RC and is formed in a wedge-like shape that is gradually narrowed along the rotational direction.

Figure 8B:
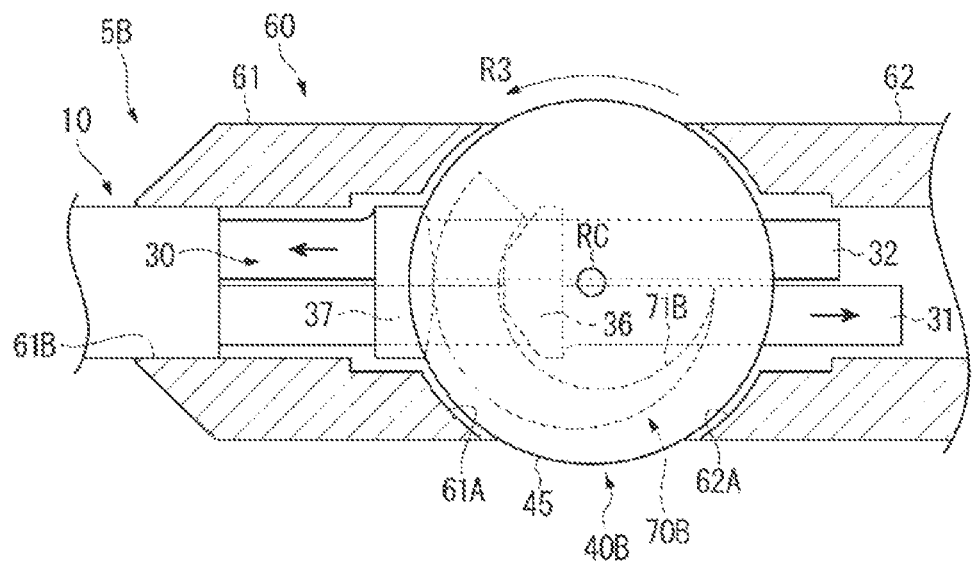

According to this configuration, when the operating member 40B is rotated in a direction R3, a first moving portion 31 is pressed by a narrowed portion 71B to move toward the proximal side, whereas a second moving portion 32 is pressed by the narrowed portion 71B to move toward the distal side, as illustrated in FIG. 8B. Consequently, bending portions 35 are bent downward, and the distal side of the elongate member 10 is thereby bent downward.

Modification Example 3

Figure 9A:
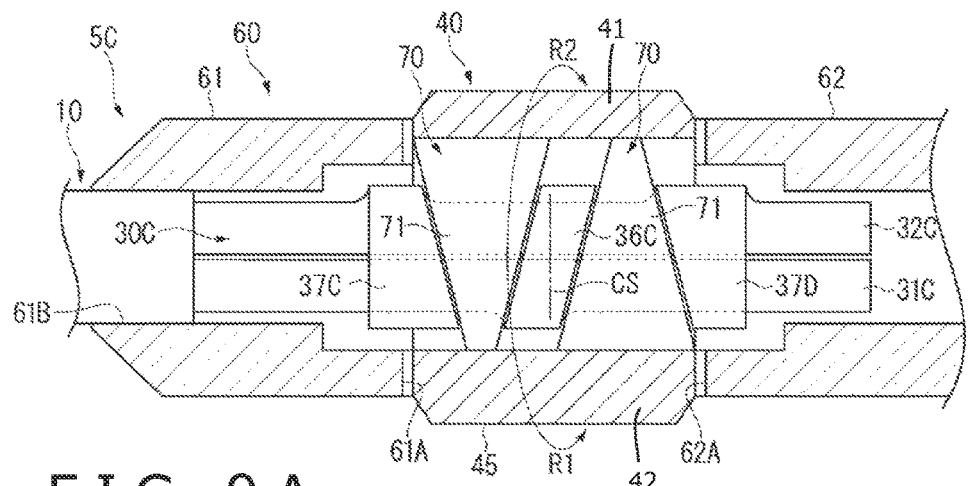
FIGS. 9A and 9B are side sectional views of an actuating member of a medical device according to a Modification Example 3.

The actuating member 5C shown in FIG. 9A differs from the first embodiment in that the actuating member 5C has a push/pull member 30C and two advancing members 70.

The advancing members 70 are accommodated in an operating member 40 in an alternate arrangement such that their narrowed portions 71 face in opposite directions.

The push/pull member 30C includes a first moving portion 31C and a second moving portion 32C. Note that with regard to other features of the configuration, the push/pull member 30C is the same as the push/pull member 30.

The first moving portion 31C has a first sliding contact portion 36C with which the advancing members 70 on the distal side and the proximal side make sliding contact. The first sliding contact portion 36C is provided to circumferentially surround the first moving portion 31C and the second moving portion 32C, is fixed to a peripheral surface of the first moving portion 31C, and retains the second moving portion 32C so that the second moving portion 32C can advance/retract. The first sliding contact portion 36C is provided, on both sides with respect to the axial direction, with first inclined surfaces, which are inclined to the same side relative to an orthogonal plane CS and are parallel to each other. The narrowed portions 71 of the advancing members 70 make sliding contact with the first inclined surfaces.

The second moving portion 32C includes a second sliding contact portion 37C with which the advancing member 70 on the distal side makes sliding contact, and a third sliding contact portion 37D with which the advancing member 70 on the proximal side makes sliding contact. The second and third sliding contact portions 37C and 37D circumferentially surround the first moving portion 31C and the second moving portion 32C, are fixed to a peripheral surface of the second moving portion 32C, and retain the first moving portion 31C so that the first moving portion 31C can advance/retract. The second sliding contact portion 37C is provided on the distal side compared to the two advancing members 70. The second sliding contact portion 37C is provided with a second inclined surface that is inclined against the orthogonal plane CS, and extends toward the opposite side compared to the inclined surface of the first sliding contact portion 36C. The narrowed portion 71 of the advancing member 70 on the distal side makes sliding contact with the second inclined surface. The third sliding contact portion 37D is provide on the proximal side relative to the two advancing members 70. The third sliding contact portion 37D is provided with a third inclined surface that is inclined against the orthogonal plane CS, and extends toward the opposite side compared to the first inclined surface of the first sliding contact portion 36C (toward the same side compared to the second inclined surface of the second sliding contact portion 37C). The narrowed portion 71 of the advancing member 70 on the proximal side makes sliding contact with the third inclined surface.

Figure 9B:
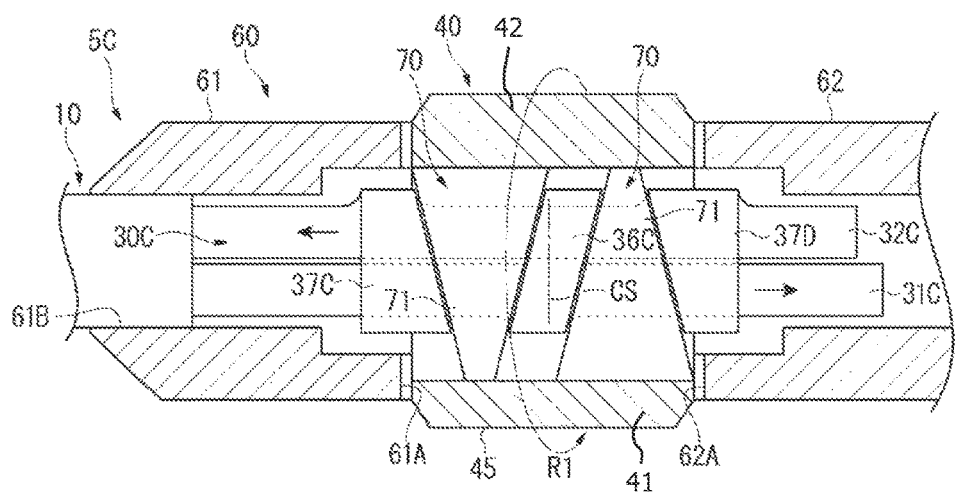

According to this configuration, when the operating member 40 is rotated in a direction R1, the advancing member 70 on the distal side is pressed toward the side of a thin-walled portion 41 of the operating member 40 by a thick-walled portion 42 of the operating member 40, resulting in its narrowed portion 71 advancing in between the first sliding contact portion 36C and the second sliding contact portion 37C, as shown in FIG. 9B. On the other hand, the advancing member 70 on the proximal side is also pressed toward the side of the thin-walled portion 41 of the operating member 40 by the thick-walled portion 42 of the operating member 40, and its narrowed portion 71 retracts between the first sliding contact portion 36C and the third sliding contact portion 37D. As a result, the second sliding contact portion 37C and the third sliding contact portion 37D are moved toward the distal side whereas the first sliding contact portion 36C is moved toward the proximal side, whereby the first moving portion 31C is moved toward the proximal side and the second moving portion 32C is moved toward the distal side. Accordingly, bending portions 35 are bent downward, and the distal side of an elongate member 10 is thereby bent downward.

Modification Example 4

Figure 10A:
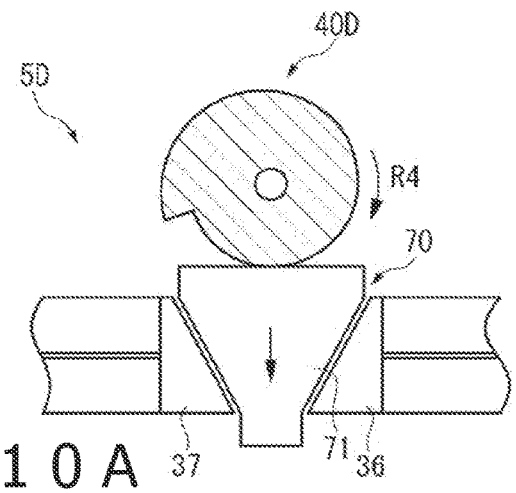
FIG. 10A is a side sectional view of an actuating member of a medical device according to a Modification Example 4.

The actuating member 5D shown in FIG. 10A differs from the first embodiment in that the actuating member 5D has an operating member 40D.

The operating member 40D is formed in a disk-like shape having an outer peripheral surface whose radius of curvature increases gradually.

According to this configuration, when the operating member 40D is rotated in a direction R4, a narrowed portion 71 advances in between a first sliding contact portion 36 and a second sliding contact portion 37, in the same manner as in the first embodiment, and the distal side of an elongate member 10 is thereby bent downward.

Modification Example 5

Figure 10B:
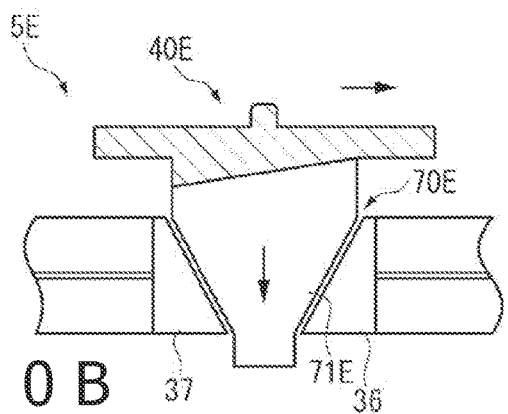
FIG. 10B is a side sectional view of an actuating member of a medical device according to a Modification Example 5.

The actuating member 5E shown in FIG. 10B differs from the first embodiment in that the actuating member 5E includes an operating member 40E and an advancing member 70E.

The advancing member 70E has an end surface on the proximal side formed to be inclined against the horizontal direction.

The operating member 40E has an inclined surface that corresponds to the inclined surface on the proximal side of the advancing member 70E, and is provided to be slidable in the axial direction of an elongate member 10.

According to this configuration, when the operating member 40E is slid toward the proximal side, a narrowed portion 71E advances in between a first sliding contact portion 36 and a second sliding contact portion 37, in the same manner as in the first embodiment, whereby the distal side of the elongate member 10 is bent downward.

Modification Example 6

Figure 10C:
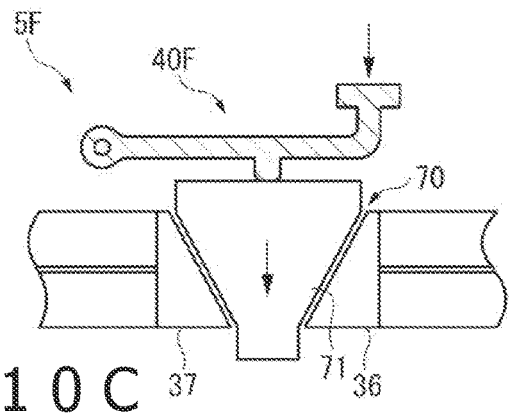
FIG. 10C is a side sectional view of an actuating member of a medical device according to a Modification Example 6.

The actuating member 5F shown in FIG. 10C differs from the first embodiment in that the actuating member 5F has an operating member 40F.

The operating member 40F is provided to be pivotally movable about one end thereof.

According to this configuration, when the other end of the operating member 40F is pressed down, a narrowed portion 71 advances in between a first sliding contact portion 36 and a second sliding contact portion 37, in the same manner as in the first embodiment, whereby the distal side of an elongate member 10 is bent downward.

Note that the present disclosure is not limited to the aforementioned embodiments and modification examples, and that various changes, improvements and the like could be effected therein by one skilled in the art without departing from the spirit or scope of the disclosure as defined in the appended claims.

For instance, a configuration may be adopted wherein the first moving portion 31 or 31C is provided with the second sliding contact portion, whereas the second moving portion 32 or 32C is provided with the first sliding contact portion.

In addition, the first inclined surface, the second inclined surface and the third inclined surface are not indispensable to the first sliding contact portion 36 or 36C, the second sliding contact portion 37 or 37C, and the third sliding contact portion 37D. The inclined surfaces may not be provided so long as the narrowed portion 71, 71A, 71B, 71E or 81 can advance in between the first sliding contact portion 36 or 36C and the second sliding contact portion 37 or 37C or in between the first sliding contact portion 36 or 36C and the third sliding contact portion 37D.

The first sliding contact portion 36 or 36C, the second sliding contact portion 37 or 37C, and the third sliding contact portion 37D may be provided in the moving portions 31 and 32 or 31C and 32C through additive members.

The narrowed portion 71, 71A, 71B, 71E or 81 may be of an arbitrary type, so long as the first moving portion 31 or 31C and the second moving portion 32 or 32C can be thereby moved relative to each other along the axial direction of the elongate member 10. For example, a configuration may be adopted wherein the narrowed portion 71 is formed in a conical shape, and the first sliding contact portion 36 and the second sliding contact portion 37 are formed in shapes corresponding to the narrowed portion. In this case, the narrowed portion and each sliding contact portion may be put into screw engagement with each other around an axis of the narrowed portion, or an end portion in the axial direction of the narrowed portion and the base portion 60 may be put into screw engagement with each other, in such a manner that the advancing member can advance/retract. According to this configuration, when the advancing member is rotated about the axis of the narrowed portion, the narrowed portion is screwed in between the first sliding contact portion and the second sliding contact portion, and the first moving portion and the second moving portion are moved in the axial direction of the elongate member 10.

Furthermore, moving characteristics of the moving portions 31 and 32 or 31C and 32C in response to rotation of the operating member 40, 40A, 40B, 40D, 40E, 40F or 90 can be set arbitrarily according to the shape of the narrowed portion 71, 71A, 71B, 71E or 81, and, hence, the moving characteristics of the moving portions 31 and 32 or 31C and 32C can be set precisely.

The push/pull member 30 or 30C may not have the connecting portion 39. In this case, for example, when an end portion on the distal side (with respect to the axial direction of the elongate member 10) of the bending portion 35 is connected to the elongate member 10, the elongate member 10 can be bent.

In addition, the elongate member 10 may have any configuration that permits the elongate member 10 to be bent.

The push/pull member 30 or 30C may not have the sealing portion 50. According to this configuration, a treatment device can be inserted and passed from the proximal side of the base portion 60 and through the lumen defined by the push/pull member 30 or 30C, so that a part on the distal side beyond the connecting portion 39, of a body lumen or cavity, can be treated.

The present disclosure is applicable not only to medical devices for use in diagnosis or treatment of paranasal sinus but also to any other medical devices that have a bendable elongate body.

What is claimed is:

1. An actuating member for making a flexible elongate member for medical use perform a predetermined action, the actuating member comprising:
    a push/pull member comprising:
        a first moving portion and a second moving portion that are disposed on a proximal side in an axial direction of the elongate member and that are movable relative to each other in the axial direction of the elongate member, wherein the first moving portion comprises a first sliding contact portion, and the second moving portion comprises a second sliding contact portion,
        a first extending portion that extends from the first moving portion toward a distal side in the axial direction of the elongate member, and
        a second extending portion that extends from the second moving portion toward the distal side in the axial direction of the elongate member,
        wherein the push/pull member is configured to be pushed and pulled in the axial direction of the elongate member in conjunction with a movement of the first moving portion and the second moving portion;
    an operating member configured to effect the movement of the first moving portion and the second moving portion; and
    an advancing member comprising a narrowed portion that gradually narrows toward an end portion, the narrowed portion being configured to advance in between and slide against the first sliding contact portion and the second sliding contact portion in conjunction with an operation of the operating member to thereby move the first moving portion and the second moving portion,
    wherein the advancing member is configured to rotate in a circumferential direction of the elongate member, and rotation of the advancing member makes the narrowed portion advance and retract, and
    wherein the push/pull member is configured to make the elongate member perform at least a bending action by transmitting the movement of the first moving portion and the second moving portion, which are moved by the advancing member, to the elongate member, and
    wherein the advancing member is configured to move the first moving portion and the second moving portion in opposite axial directions, and the movement of the first moving portion and the second moving portion makes the elongate member perform the bending action.

2. The actuating member according to claim 1, wherein the operating member comprises a tube-shaped member,
    wherein the advancing member is disposed on an inner peripheral surface of the tube-shaped member in the circumferential direction, and
    wherein rotation of the operating member makes the advancing member rotate.

3. The actuating member according to claim 1, wherein the actuating member further comprises a visual recognition portion that enables at least a bending amount of the elongated member to be confirmed by visual recognition.

4. The actuating member according to claim 3, wherein the visual recognition portion comprises a marker or a scale.

5. A medical device comprising:
    the actuating member according to claim 1; and
    a flexible elongate member, wherein the actuating member is configured to make the flexible elongate member perform at least the bending action.

* * * * *